United States Patent [19]
Hafler et al.

[11] Patent Number: 6,162,609
[45] Date of Patent: Dec. 19, 2000

[54] DIAGNOSTIC AND THERAPEUTIC METHODS BASED UPON Vα24JαQT CELLS

[75] Inventors: David A. Hafler, West Newton; Jack L. Strominger; Brian Wilson, both of Lexington; Sally C. Kent, Brighton, all of Mass.

[73] Assignee: The Brigham and Women's Hospital, Inc., Boston, Mass.

[21] Appl. No.: 09/213,285

[22] Filed: Dec. 17, 1998

Related U.S. Application Data

[60] Provisional application No. 60/070,298, Dec. 31, 1997.

[51] Int. Cl.$^7$ ..................................................... G01N 33/53
[52] U.S. Cl. .......................... 435/7.24; 435/7.92; 435/29; 435/372.3; 530/351
[58] Field of Search ................................. 435/7.24, 7.92, 435/29, 372.3; 530/351

[56] References Cited

FOREIGN PATENT DOCUMENTS

WO 94/19470   9/1994   WIPO .............................. C12N 15/62

OTHER PUBLICATIONS

The Murck Manual, 16$^{th}$ Ed, 1992, pp. 339–342.
Takayuki, et al., "Selective Reduction of T Cells Bearing Invariant Vα24JαQ Antigen Receptor in Patients with Systemic Sclerosis," *J.Exp. Med.* 182:1163–1168 (1995).
International Search Report for PCT/US98/26868.
Abbas, et al., "Functional Diversity of Helper T Lymphocytes," *Nature* 383:787–793 (1996).
Baxter, et al., "Association Between αβTCR$^+$ CD4$^-$CD8$^-$ T–Cell Deficiency and IDDM in NOD/Lt Mice," *Diabetes* 46:572–582 (1997).
Bendelac, et al., "Mouse CD1–Specific NK1 T Cells: Development, Specificity, and Function," *Annu. Rev. Immunol.* 15:535–62 (1997).
Brown, et al., "β2–Microglobulin–Dependent NK1. 1$^+$ T Cells Are Not Essential for T Helper Cell 2 Immune Responses," *J. Exp. Med.* 184:1295–1304 (1996).
Chen, et al., "Impaired NK1$^+$ T Cell Development and Early IL–4 Production in CD1–Deficient Mice," *Immunity* 6:459–467 (1997).
Davodeau, et al., "Close Phenotypic and Functional Similarities Between Human and Murine αβ T Cells Expressing Invariant TCR α–Chains," *J. Immunol.* 158:5603–5611 (1997).
Denkers, et al., "A Role for CD4$^+$NK1.1$^+$ T Lymphocytes as Major Histocompatibility Complex Class II Independent Helper Cells in the Generation of CD8$^+$ Effector Function against Intracellular Infection," *J. Exp. Med.* 184:131–139 (1996).
Exley, et al., "Requirements for CD1d Recognition by Human Invariant Vα24$^+$ CD4$^-$CD8$^-$ T Cells," *J. Exp. Med.* 186:109–120 (1997).
Fox, et al., "IL–4 Expression at the Onset of Islet Inflammation Predicts Nondestructive Insulitis in nonobese Diabetic Mice," *J. Immunol.* 158:2414–2424 (1997).
Gombert, et al., "IL–7 Reverses NK1$^+$ T Cell–Defective IL–4 Production in the Non–Obese Diabetic Mouse," *Intl. Immunol.* 8:1751–1758 (1996).
Kallmann, et al., "Systemic Bias of Cytokine Production Toward Cell–Mediated Immune Regulation in IDDM and Toward Humoral Immunity in Graves'Disease," *Diabetes* 46:237–243 (1997).
Lanier, et al., "Human NKR–P1A: A Disulfide–Linked Homodimer of the C–Type Lectin Superfamily Expressed by a Subset of NK and T Lymphocytes," *J. Immunol.* 153:2417–2428 (1994).
Mendiratta, et al., "CD1d1 Mutant Mice Are Deficient in Natural T Cells That Promptly Produce IL–4," *Immunity* 6:469–477 (1997).
Mieza, et al., "Selective Reduction of Vα14$^+$ NK T Cells Associated with Disease Development in Autoimmune–Prone Mice," *J. Immunol.* 156:4035–4040 (1996).
Mueller, et al., "Pancreatic Expression of Interleukin–4 Abrogates Insulitis and Autoimmune Diabetes in Nonobese Diabetic (NOD) Mice," *J. Exp. Med.* 184:1093–1099 (1996).
Porcelli, et al., "Analysis of T Cell Antigen Receptor (TCR) Expression by Human Peripheral Blood CD4$^-$8$^-$ α/β T Cells Demonstrates Preferential Use of Several Vβ Genes and an Invariant TCR α Chain," *J. Exp. Med.* 178:1–16 (1993).
Rapoport, et al., "Interleukin 4 Reverses T Cell Proliferative Unresponsiveness and Prevents the Onset of Diabetes in Nonobese Diabetic Mice," *J. Exp. Med.* 178:87–99 (1993).
Smiley, et al., "Immunoglobulin E Production in the Absence of Interleukin–4–Secreting CD1–Dependent Cells," *Science* 275:977–979 (1997).
Takeda, et al., "The Development of Autoimmunity in C57BL/6 lpr Mice Correlates with the Disappearance of Natural Killer Type 1–Positive Cells: Evidence for Their Suppressive Action on Bone Marrow Stem Cell Proliferation, B Cell Immunoglobulin Secretion, and Autoimmune Symptoms," *J. Exp. Med.* 177:155–164 (1993).
Verge, et al., "Prediction of Type I Diabetes in First–Degree Relatives Using a Combination of Insulin, GAD, and ICA512bdc/IA–2 Autoantibodies," *Diabetes* 45:926–933 (1996).
Vicari, et al., "Mouse NK1.1$^+$ T Cells: A New Family of T Cells," *Immunology Today* 17:71–76 (1996).
von Herrath, et al., "Interfeon–γ Is Essential for Destruction of β Cells and Development of Insulin–Dependent Diabetes Mellitus," *J. Exp. Med.* 185:531–539 (1997).

*Primary Examiner*—Patrick Nolan
*Attorney, Agent, or Firm*—Michael A. Sanzo; Pillsbury Madison & Sutro LLP

[57] ABSTRACT

The present invention is directed to methods that can be used for diagnosing whether an individual either has, or is likely to develop, an autoimmune disease. The methods are based upon determining the level of CD4$^-$CD8$^-$ Vα24JαQ$^+$ T cells present in the individual being tested or the pattern of cytokine secretion evidenced by these cells. In addition, the invention is directed to a therapeutic method for treating or preventing autoimmune disease which is based upon the specific expansion of the CD4$^-$CD8$^-$ Vα24JαQ$^+$ T cell population.

5 Claims, No Drawings

SEQUENCE LISTING

<160> NUMBER OF SEQ ID NOS: 2

<210> SEQ ID NO 1
<211> LENGTH: 4
<212> TYPE: PRT
<213> ORGANISM: Homo sapiens

<400> SEQUENCE: 1

Cys Val Val Ser
 1

<210> SEQ ID NO 2
<211> LENGTH: 5
<212> TYPE: PRT
<213> ORGANISM: Homo sapiens

<400> SEQUENCE: 2

Asp Arg Gly Ser Thr
 1               5

DIAGNOSTIC AND THERAPEUTIC METHODS BASED UPON Vα24JαQT CELLS

CROSS REFERENCE TO RELATED APPLICATIONS

The present application claims priority to U.S. provisional application Ser. No. 60/070,298, filed on Dec. 31, 1997.

FIELD OF THE INVENTION

The present invention is directed to methods for diagnosing and treating autoimmune diseases. Diagnostic methods are based upon the discovery that CD4$^-$CD8$^-$ Vα24JαQ$^+$ T cells are lost in response to the onset of disease and also develop an altered pattern of cytokine secretion. Therapeutic methods are based upon the discovery of a means for selectively expanding this subset of T cells.

BACKGROUND OF THE INVENTION

Autoimmune diseases are the result of a patient's immune system attacking their own cells and tissues. This can result in a wide variety of diseases, including multiple sclerosis, myasthenia gravis, rheumatoid arthritis, type 1 diabetes, systemic lupus erythematosus, psoriasis, scleroderma, idiopathic thrombocytopenia purpura, and Sjögen's disease. For the most part, the etiology of autoimmune diseases is poorly understood, and attempts at therapeutic intervention have met with limited success.

Recently, it has been discovered that T lymphocytes exist in subpopulations characterized by different patterns of cytokine secretion (Abbas et al., *Nature* 383:787–793 (1996)). The Th1 subset of CD4$^+$ T cells promotes inflammatory cellular immune responses and is biased toward the secretion of IFN-γ, TNF-β, and IL-2. Th2 cells are biased towards the secretion of IL-4, IL-5, IL-6, IL-10, and IL-13, induce humoral immunity, and inhibit Th1 responses. In certain autoimmune diseases, e.g., in type 1 diabetes, it appears that the Th1 pattern of secretion often becomes predominant but the cellular mechanisms integrating the drive to Th1 or Th2 are poorly understood (Kallmann et al., *Diabetes* 46:237–243 (1997)). One possibility is that disease onset is associated with an expansion or loss of groups of T cells with particular secretory characteristics.

In the mouse, a bias toward Th2 cells may be promoted by the activation of T cells having the Vα14Jα281 receptor (Bendelac et al., *Ann. Rev. Immunol.* 15:535–562 (1997); Vicari et al., *Immunol. Today* 17:71–76 (1996)). Humans have been shown to have a population of T cells expressing a receptor, Vα24JαQ, with a close sequence homology to Vα14Jα281 (Porcelli et al., *J. Exp. Med.* 178:1–16 (1993)). Defining the relationship between changes in these cells and the onset of autoimmune diseases may lead to new diagnostic and therapeutic procedures.

SUMMARY OF THE INVENTION

The present invention is based upon the discovery that there is a subset of T cells that decreases in number and which undergoes a change in its cytokine secretion pattern as humans develop autoimmune disease. Cell loss and changes in cytokine secretion become more pronounced as individuals progress from a normal to a diseased state. In addition, therapeutic procedures have been developed to prevent T cell loss and that can be used to prevent or treat autoimmune diseases.

In its first aspect, the invention is directed to a method for evaluating the likelihood that a human subject either has, or will develop, an autoimmune disease by determining the number of CD4$^-$CD8$^-$ Vα24JαQ$^+$ T cells in their circulation. This number is compared with the number of such cells present in a control group comprised of individuals known to be free of autoimmune disease and the difference between the values obtained for the tested subject and control group is then correlated with the likelihood of the subject either having or developing autoimmunity. Likelihood increases as the number of Vα24JαQ$^+$ cells in the tested subject decreases relative to the number of such cells present in the control group. Among the autoimmune diseases that may be tested for using This procedure are multiple sclerosis; systemic lupus erythematosus; rheumatoid arthritis; type 1 diabetes; myasthenia gravis; psoriasis; scleroderma; Sjögen's disease; and idiopathic thrombocytopenia purpura.

One variation of the diagnostic method described above involves the determination of the percentage of total T cells that are CD4$^-$CD8$^-$ Vα24JαQ$^+$ in the subject being tested and comparing This to the percentage of such cells in a control group of disease-free individuals. Again, the likelihood of the tested individual having or developing an autoimmune disease increases as the percentage of CD4$^-$CD8$^-$ Vα24JαQ$^+$ cells in This individual decreases relative to the percentage of these cells in the control group. One way that percentages may be determined is by sorting all CD4$^-$CD8$^-$ αβTCR$^+$ T cells using flow cytometry; amplifying Vα24 transcripts and sequencing the TCR CDR3 region of the amplified product to determine frequency; and then multiplying This frequency by the percentage of total T cells that are CD4$^-$CD8$^-$ Vα24$^+$. This procedure may be applied to the autoimmune diseases listed above and, in particular, to type 1 diabetes.

In another aspect, the present invention is directed to a method for determining the likelihood that a human subject will develop an autoimmune disease based upon the types of cytokines secreted by CD4$^-$CD8$^-$ Vα24JαQ$^+$ T cells. This method is based upon the discovery that, when isolated from normal individuals, these cells secrete substantial levels of both interferon gamma (IFN-γ) and interleukin-4 (IL-4), whereas cells from patients with autoimmune disease preferentially secrete IFN-γ. Thus, the method involves isolating CD4$^-$CD$^-$ Vα24JαQ$^+$ T cells from the test subject, determining the extent to which these cells secrete IL-4, and then correlating secretion with the likelihood of the subject having or developing an autoimnmme disease. Likelihood decreases as the secretion of IL-4 increases. Preferably, the determination of IL-4 secretion should be performed after the isolated T cells are stimulated with a T cell activating factor such as anti-CD3 antibody. Secretion levels of IL-4 in cells derived from normal individuals can be used as a basis for comparison.

The method can also be performed by determining the ratio of IL-4 to IFN-γ secretion in the isolated cells. In This case, the likelihood of an individual having or developing an autoimmune disease decreases as the ratio increases, i.e., as the levels of IL-4 rise with respect to the levels of IFN-γ. Again, the secretion ratio in cells derived from normal individuals can be used as a basis of comparison. The method can be used for detecting the autoimmune diseases discussed above and, in particular, for detecting individuals that have or are likely to develop type 1 diabetes.

In another aspect, the present invention is directed to a method of treating a human subject that has or is likely to develop an autoimmune disease by increasing the number of CD4$^-$CD8$^-$ Vα24JαQ$^+$ T cells in their circulation, preferably by exposing the cells to CD1d or a digestion product of CD1d. Clonal expansion may take place after T cells are removed from an individual, or, alternatively, the T cell subpopulation may be expanded in vivo. The therapeutic procedure may be used for multiple sclerosis, systemic lupus erythematosus, rheumatoid arthritis, type 1 diabetes, myasthenia gravis, psoriasis, scleroderma, Sjögen's disease, or idiopathic thrombocytopenia purpura.

DETAILED DESCRIPTION OF THE INVENTION

The present invention is based upon the concept that there are certain subsets of T cells that can contribute to the development of autoimmune diseases. This concept is supported by experiments performed on patients with type 1 diabetes and their non-diabetic identical siblings. The results indicate that the percentage of total T cells that are CD4$^-$CD8$^-$ V$\alpha$24J$\alpha$Q$^+$ is substantially reduced in diabetics relative to their "at-risk" non-diabetic siblings. In addition, it was found that CD4$^-$CD8$^-$ V$\alpha$24J$\alpha$Q cells cloned from the diabetics evidenced a significantly different pattern of cytokine secretion in response to stimulation with anti-CD3 antibody. Specifically, these clones were found to secrete only IFN-$\gamma$, whereas nearly all clones derived from non-diabetic siblings secrete both IL-4 and IFN-$\gamma$.

Other results indicated that the specific subset of T cells associated with the onset of autoimmune disease, i.e., the CD4$^-$CD8$^-$ V$\alpha$24J$\alpha$Q cells, proliferate rapidly when exposed to CD1d. This provides a means for expanding This T cell subset in individuals with abnormally low levels such as those that have or are at risk for developing autoimmunity.

A. Diagnostic Methods for Detecting Autoimmunity Based on the Number of CD4$^-$CD8$^-$ V$\alpha$24J$\alpha$Q$^+$ T Cells Present in an Individual There are two basic methods that may be used for determining whether a particular individual either has, or is likely to develop, an autoimmune disease. The first is based upon the number of CD4$^-$CD8$^-$ V$\alpha$24J$\alpha$Q$^+$ T cells that the individual has relative to the number found in a population of normal individuals, i.e., individuals that do not have autoimmune disease. One method that has been demonstrated to be effective for quantitating the T cell subset is to separate CD4$^-$CD8$^-$$\alpha\beta$ T cell receptor-containing cells by flow cytometry and to then amplify all V$\alpha$24 transcripts by PCR. The amplification product is sequenced to determine the frequency of V$\alpha$24J$\alpha$Q$^+$ sequences, and This frequency is then multiplied by the percentage of total T cells that are CD4$^-$CD8$^-$ V$\alpha$24$^+$ as determined by flow cytometry. The product equals the percentage of total T cells that are CD4$^-$CD8$^-$ V$\alpha$24J$\alpha$Q$^+$.

The percentage determined in the manner described above can be compared directly with similarly determined percentages in a normal population or the percentages can be readily converted into cell numbers and compared. In either case, there is a direct correlation between a decrease in This subset of T cells and either the likelihood that the subject being tested will develop an autoimmune disease or that they already have such a disease that has not yet progressed to the point where overt clinical manifestations are present. Of course, the same assay can be used to confirm a diagnosis of autoimmune disease made by other criteria.

Although the procedure described above is effective for determining whether there has been a decrease in an individual's T cells, the invention is compatible with other procedures as well. For example, antibodies specifically directed to a cell surface antigen exclusively present on V$\alpha$24J$\alpha$Q T cells may be used in standard immunoassays for quantitating cell number. Methods for making and selecting such antibodies are well known to those of skill in the art, as evidenced by standard reference works such as: Harlow et al., *Antibodies, A Laboratory Manual,* Cold Spring Harbor Laboratory, N.Y. (1988); Klein, *Immunology: The Science of Self-Non-Self Discrimination* (1982); and Kennett et al., *Monoclonal Antibodies and Hybridomas: A New Dimension in Biological Analyses* (1980). Once produced, antibodies can be used in radioimmunoassays or immunometric assays, also known as "two site" or "sandwich" assays (see Chard, "An Introduction to Radioimmune Assay and Related Techniques," in *Laboratory Techniques in Biochemistry and Molecular Biology,* North Holland Publishing Co., N.Y. (1978)). In a typical immunometric assay, a quantity of unlabeled antibody is bound to a solid support that insoluble in the fluid being tested, e.g., blood, lymph, cellular extracts, etc. After the initial binding of antigen to immobilize antibody, a quantity of detectably labeled second antibody (which may or may not be the same as the first) is added to permit detection and/or quantitation of bound antigen (see, e.g., Radioimmune Assay Method, Kirkham et al., ed., pp. 199–206, E & Livingstone, Edinburogh (1970)). Many variations of these types of assays are known in the art and could be used to quantitate V$\alpha$24J$\alpha$Q$^+$ cells. Binding assays could also be performed using a labeled ligand that binds specifically to the V$\alpha$24J$\alpha$Q$^+$ cells. As examined further in the Examples section, labeled CD1d protein, or fragments of This protein, should be suitable for This purpose.

B. Diagnostic Methods for Detecting Autoimmunity Based on the Cytokine Secretion Pattern of CD4$^-$CD8$^-$ V$\alpha$24J$\alpha$Q$^+$ T Cells An alternative method for determining whether an individual has, or is likely to develop, an autoimmune disease is based upon the cytokines secreted by CD4$^-$CD8$^-$ V$\alpha$24J$\alpha$Q$^+$ T cells. It has been experimentally demonstrated that the onset of autoimmune disease is associated with a decrease in IL-4 secretion by these cells relative to secretion seen in cells derived from normal individuals. Secretion of IFN-$\gamma$ by the cells is relatively unchanged. Thus, a determination may be made either of IL-4 secretionper se, or the ratio of IL-4 secretion relative to IFN-$\gamma$ secretion. In either case, best results are obtained when cells are stimulated with a factor such as anti-CD3 antibody.

The first step in the procedure requires that the relevant cells be sorted using flow cytometry and commercially available antibodies and that the sorted cells be grown to determine if they have the V$\alpha$24J$\alpha$Q form of receptor. The identified clones may then be stimulated with commercially available anti-CD3 antibody and supernatants, then assayed for IL-4 concentration and, if desired, IFN-$\gamma$ concentration. In each case, This may be accomplished using ELISA assays. As discussed in the Examples section, there is a close correlation between a bias toward IFN-$\gamma$ secretion by the cells and autoimmune disease, particularly type 1 diabetes.

C. Expansion of V$\alpha$24J$\alpha$Q Cells as a Therapy

It has been demonstrated that CD4$^-$CD8$^-$ V$\alpha$24J$\alpha$Q$^+$ cells can be clonally expanded by exposing the cells to CD1d. Thus, individuals that are identified as having abnormally reduced levels of these cells and therefore being at risk for the development of an autoimmune disease, may be treated using either This protein or peptides derived from the protein. For example, T cells may be isolated from a patient, exposed to transfectants expressing CD1d to increase the proportion of CD4$^-$CD8$^-$ V$\alpha$24J$\alpha$Q$^+$ cells, and then reintroduced into the patient.

An alternative, and generally preferable method, is to treat an individual directly by injecting CD1d or a T-cell activating fragment derived from This protein. The exact dosage to be given to a patient will be determined using standard clinical techniques and the effect of administration will be followed using periodic assays to determine whether CD4$^-$CD8$^-$ V$\alpha$24J$\alpha$Q$^+$ cells have increased in number. Once cells have reached a level typical of that present in normal individuals, administration should cease and the patient should be monitored to determine if levels again fall. If This occurs, more therapeutic agent may be administered.

Any route of administration and dosage form is compatible with the present invention and T cell stimulatory agent may be administered either as the sole active agent or in combination with other therapeutically active drugs. In general, non-oral routes of administration are preferred in order to avoid the degradation of CD1d. All dosage forms, whether tablets, pills, capsules, powders, aerosols, suppositories, skin patches, or parenterals, may be prepared using methods that are standard in the art (see, e.g., *Remington's Pharmaceutical Sciences,* 16th ed., A. Oslo, editor, Easton, Pa. (1980)) and dosage forms may be prepared in conjunction with any of the vehicles and excipients commonly employed in pharmaceutical preparations, e.g., talc, gum arabic, lactose, starch, magnesium sterate, cocoa butter, aqueous or non-aqueous solvents, oils, paraffin derivatives, glycols, etc. Coloring and flavoring agents may also be added to preparations, particularly to those for oral administration.

D. Utility

The present invention provides a means for determining the likelihood that an individual will develop an autoimmune disease such as type 1 diabetes or multiple sclerosis. The test can be used for patients with a family history of autoimmune disease or it can be used for screening the population at large. Once an individual is identified as having abnormally low levels of CD4$^-$CD8$^-$ V$\alpha$24J$\alpha$Q$^+$ cells, they can be monitored more closely and administered agents designed to treat or prevent the progression of autoimmunity. The results reported herein suggest that the diagnostic methods are highly reliable as a predictor of disease progression and onset, and that specific expansion of cells as a therapy can be achieved using CD1d.

EXAMPLES

I. Materials and Methods

Antibodies and phenotypic analyses of T cells. Flow cytometry experiments were performed on FACScaliber and FACS Vantage instruments, Becton Dickinson. Monoclonal antibody (mAb) DX1 was a gift of Dr. L. Lanier. Antibodies anti-CD4, anti-CD8, anti-panTCR, were purchased from Becton Dickinson. Antibodies anti-V$\alpha$24, anti-CD8$\beta$, anti-CD56, anti-CD16, anti-p58KIR (NK workshop mAbs GL183 and EB6) were from Immunotech. Anti-CD69 and anti-CD94 were from Pharmingen.

CDR3 TCR sequencing. Total CD4$^-$CD8$^-$V$\alpha$24J$\alpha$Q CDR3 sequences were amplified by RT-PCR using V$\alpha$24 and constant region specific primers as described previously (Porcelli et al., *Journal of Experimental Medicine* 178:1–16 (1993)), and cloned using a Stratagene pCR-Script™ kit. TCR transcripts from individual T cell clones were amplified by RT-PCR. Sequences for plasmid and PCR DNA products were determined directly on an ABI373A Automated DNA Sequencer.

Cell culture and cytokine assay. Single cell sorts were grown on allogeneic feeders at 50,000/well and 721.221 cells at 5000/well, irradiated (5000 rads), supplemented with 1 $\mu$g/ml, PHA-P, IL-2 and IL-7 each at 10 U/mL, and propagated as described (Fukaura et al., *Journal of Clinical Investigation* 98:70–77 (1996)). Clones positive for V$\alpha$24 and NKR-P1A by flow cytometry and a V$\alpha$24J$\alpha$Q CDR3 TCR sequence were assayed for cytokine secretion. Cells were stimulated (25,000/well) with plate-bound anti-CD3 (1 $\mu$g/mL, Immunotech) or control isotype antibody (Sigma) for 4, 8, or 24 hours. Supernatants were collected and assayed for IL-4 and IFN-$\gamma$ by capture ELISA. After 24 hours, 1 $\mu$Ci/well of [$^3$H-]thymidine was added and incorporation measured as described (Fukaura et al., *Journal of Clinical Investigation* 98:70–77 (1996)).

CD1 restriction. Restriction experiments using CD1 isoform (CD1a, CD1c, CD1d, and pSR$\alpha$-neo vector alone) transfected C1R cells was performed as described (Davodeau et al., *Journal of Immunology* 158:5603–5611 (1997)).

II. Results and Discussion

To determine if there was a relationship between the number of circulating CD4$^-$CD8$^-$ V$\alpha$24J$\alpha$Q$^+$ T cells and type 1 diabetes, a frequency analysis was performed on a set of type 1 diabetes discordant monozygotic twins and triplets. The number of circulating CD4$^-$CD8$^-$ V$\alpha$24J$\alpha$Q$^+$ T cells present in diabetes-free twins/triplets was compared with those present in their siblings with disease. The percentage of circulating invariant CD4$^-$CD8$^-$ V$\alpha$24J$\alpha$Q T cells could be determined by multiplying the frequency of invariant V$\alpha$24J$\alpha$Q sequences present in the total CD4$^-$CD8$^-$ V$\alpha$24$^+$ population times the percent of CD4$^-$CD8$^-$ V$\alpha$24$^+$ T cells as measured by flow cytometry analysis (Table 1). No CD4$^-$CD8$^-$ V$\alpha$24J$\alpha$Q$^+$T cells were detected in three diabetics despite at least three sorting attempts for each subject. The percentage of CD4$^-$CD8$^-$ V$\alpha$24J$\alpha$Q$^+$ T cells in a previously disease-free diabetic twin (patient 6A, Table 1) studied the week of IDDM diagnosis was similar to their long-term IDDM twin and the other diabetics. In all sets of family pairings, the IDDM sibling had markedly lower percentages of CD4$^-$CD8$^-$ V$\alpha$24J$\alpha$Q$^+$ T cells (P=0.015, paired sign test using only the discordant twins/triplets data).

To determine whether human V$\alpha$24J$\alpha$Q$^+$ T cells were functionally altered in at-risk for and type 1 diabetics, single CD4$^-$ and CD8$^-$ mononuclear cells expressing the V$\alpha$24$^+$ TCR were cloned. The initial analysis was carried out on clones generated from the IDDM non-progressing member of a sibling pair, subject 7A (Table 1). All clones expressed the invariant V$\alpha$24J$\alpha$Q junctional sequences conserving the germ line encoded amino acids V$\alpha$24 (–CVVS: SEQ ID NO: 1) and J$\alpha$Q (:DRGST– SEQ ID NO: 2). Eight of ten clones were V$\beta$11+ and two were V$\beta$13+. All of the clones were CD4$^-$, and uniformly negative when stained for the CD8$\beta$-chain. Surface expression for CD8$\alpha\alpha^+$ appeared to reflect activation state, as staining for This marker reverted to negative 2–3 weeks post-stimulation. All T cells expressed the human homologue of the murine NK1.1 molecule. NKP-P1A (Lanier et al., *Journal of Immunology* 153:2417–2428 (1994)), and the C-type lectins encoded by the NK locus, CD69 and CD94.

CD1d restriction was assessed by co-cultivating the V$\alpha$24J$\alpha$Q$^+$ T-cell clones with C1R cells transfected with a CD1d or control expression vector (Exley, et al., *J. Exp. Med.* 1861–11 (1997)). A T-cell clone (4.2) with a non-invariant TCR $\alpha$-chain (V$\alpha$24N3J$\alpha$6) was included as a negative control. All T-cell clones except 3.5, 3.8, and the control clone 4.2 specifically proliferated in response to the CD1d transfectant. All of the clones except 3.5 and 4.2 secreted IL-4 and IFN-$\gamma$ in a CD1d specific manner. Clone 3.5 secreted only IFN-$\gamma$ in response to CD1d. The fine specificity of the clones for CD1d was tested by using C1R targets transfected with either CD1a, CD1c, CD1d, or vector alone. Only CD1d-expressing target cells specifically stimulated each of the CD4$^-$CD8$^-$ V$\alpha$24J$\alpha$Q$^+$ clones as assessed by IL-4 and IFN-$\gamma$ secretion.

A panel of V$\alpha$24J$\alpha$Q$^+$ T-cell clones was raised from: 1) the twins/triplets discordant for type 1 diabetes (see Table 1); 2) from an additional four at-risk non-progressors with elevated serum IL-4 levels; and 3) two haplotype (DR3/DR2 and DR4/DRX) matched normal controls. Twenty-five out of 28 clones raised from the at-risk non-progressors among the discordant twins/triplets secreted both IL-4 and IFN-$\gamma$ (>10 pg/ml) on stimulation with anti-CD3. The other three clones produced only IFN-$\gamma$. Unlike the other non-progressing twins, only one clone from the triplet 1A secreted modest amounts of IL-4 when stimulated. Only a single attempt to generate clones from This subject was made due to their subsequent entry into a clinical trial. All of the 56 clones raised from the diabetic twins/triplets secreted only IFN-$\gamma$ with anti-CD3 stimulation, and diabetic twins 4B and 5B had no identifiable CD4$^-$CD8$^-$ V$\alpha$24J$\alpha$Q$^+$ T cells (Table 1). There was no difference in the proliferative response to anti-CD3 between the clones raised from diabetics or other subjects. The new onset type 1 twin 6A (Table 1) had 9/9 CD4⁻CD8⁻ Vα24JαQ⁺ T-cell clones that secreted only IFN-γ. This suggests that the Th1 phenotype seen in the new onset twin was not related to duration of diabetes but occurred prior to, or concurrent with, the onset of overt disease.

An additional set of 33 clones were generated from four at-risk non-progressors and 18 clones raised from MHC haplotype matched controls. Clones raised from these subjects were phenotypically similar to the diabetes-free twins and a series of invariant Vα24JαQ⁺ T-cell clones previously described (Exley et al., *J. Exp. Med.* 186:1–11 (1997); Davodeau et al., *J. Immunol.* 158:5603–5611 (1997)). Thus, all Vα24JαQ T-cell clones raised from type 1 patients showed an extreme Th1 bias, making them incapable of providing the IL-4 necessary for the initiation of Th2 responses. In fact, unopposed IFN-γ secretion should promote a strong cellular immune response, and could augment or initiate a Th1-dominated cellular attack on β cells (von Herrath et al., *J. Exp. Med.* 185:531–539 (1997); Denkers et al., *J. Exp. Med.* 184:131–139 (1996)).

The functional studies on the Vα24JαQ⁺ T cells from the discordant twins/triplets, at-risk non-progressors, and controls suggested that these two groups had polarized cell mediated immune responses. To further assess This possibility, serum IL-4 and IFN-γ were determined in 14 at-risk IDDM non-progressors who had remained IDDM-free despite a 50% risk of having developed diabetes during the period of study (Verge et al., *Diabetes* 45:926–933 (1996)). This cohort was defined by having remained healthy despite five or more years follow-up after diagnosis of type 1 diabetes in a first degree relative and being islet cell antibody+ (ICA+) with any two of the following autoantibodies: anti-GAD, anti-IA2, or insulin autoantibodies. Seven of 14 type 1 non-progressors had markedly elevated levels of serum IL-4, six of whom also had elevated IFN-γ (0.2–35 ng/ml). Despite the elevation of cytokines in the serum from 7 of 14 non-progressors, all seven IL-4⁺ individuals have remained healthy with no evidence of chronic infectious, or atopic/allergic illnesses. The remaining 7 had levels for both cytokines below the detection limit of the ELISA (0.015 ng/ml). Five of 14 individuals in this group were found to have the strongly protective MHC allele DQB1*0602 and therefore are not at the same risk of progression as the remaining nine members of this cohort (Pugliese et al., *Diabetes* 44:608–613 (1995)). Three of these five individuals had elevated serum IL-4 and IFN-γ levels. This was in contrast to the finding that IL-4 could not be detected in the serum (before or after diagnosis of type 1 diabetes) in 12 individuals with identical autoantibody status who developed IDDM after five or more years of follow-up.

Elevated cytokines were also detected in archival serum samples obtained from 3/23 individuals at the time of diagnosis of type 1 diabetes and in 5/26 type 2 diabetics who did not have autoantibodies or a family history of type 1 diabetes. When compared to either normals, antibody positive first degree relatives, recent onset diabetics, long-term diabetics (IDDM>2 years), autoantibody negative first degree relatives, or untreated multiple sclerosis patients (MS), the frequency of serum IL-4⁺ individuals was significantly elevated in the non-progressor cohort. The authenticity of the detected IL-4 was independently confirmed by using another set of ELISA antibodies, binding to soluble recombinant IL-4 receptor produced in insect cells, and by Western blot.

The results demonstrate a relationship between elevated serum IL-4 levels and resistance to progression of an autoimmune disorder. Prolonged hyperglycemia as an explanation for the absence of IL-4 in type 1 diabetics seems less likely since IL-4 was detected in the serum of type 2 diabetics. The presence of elevated IL-4 levels was not an absolute predictor of IDDM resistance since only half of the resistant cohort had elevated serum IL-4 levels, as did 3/23 diabetics on or about the time of diagnosis.

In the NOD mouse, compelling evidence exists that IL-4 exerts a dominant negative effect on progression to IDDM (Rapoport et al., *J. Exp. Med.* 178:87–99 (1993); Mueller et al., *J. Exp. Med.* 184:1093–1099 (1996); Fox et al., *J. Immunol.* 158:2414–2424 (1997)). Differentiation of T cells into IL-4 secreting Th2 effector cells requires IL-4 priming (Abbas et al., *Nature* 383:787–793 (1996)). While this proposed function for NK1.1⁺ T cells was not obligatory for all Th2 immune responses (Bendelac et al., *Ann. Rev. Immunol.* 15:535–562 (1997); Brown et al., *J. Exp. Med.* 184:1295–1304 (1996); Smiley et al., *Science* 275:977–979 (1997)), T cell IL-4 secretion was noted to be markedly diminished in a CD1 knockout background (Smiley et al., *Science* 275:977–979 (1997); Chen et al., *Immunity* 6:459–467 (1997); Mendiratta et al., *Immunity* 6:469–477 (1997)). NK1.1⁺ T cells were present in diminished numbers and decreased in frequency prior to the onset of disease in several murine models of autoimmunity (Bendelac et al., *Ann. Rev. Immunol.* 15:535–562 (1997); Vicari et al., *Immunology Today* 17:71–76 (1996); Takeda et al., *J. Exp. Med.* 177:155–164 (1993); Mieza et al., *J Immunol.* 156:4035–4040 (1996); Gombert et al., *Int'l Immunol.* 8:1751–1758 (1996)). In these models, autoimmunity was temporally accelerated by depletion of NK1.1⁺ T cells and delayed by generating mice transgenic for the Vα14Jα281 TCR. Diabetes was also prevented in the NOD mouse by adoptive transfer of a population harboring the NK1.1-like class of T cell (Baxter et al., *Diabetes* 46:572–582 (1997)).

In summary, type 1 diabetes was associated with an extreme Th1 phenotype for Vα24JαQ⁺ T cells and a decrease in their circulating frequency. The data presented herein provide a strong link between Vα24JαQ⁺T cells and human type 1 diabetes, suggesting that they are functionally related to the resistance or progression of This autoimmune disease in humans.

TABLE 1

| Twins/Triplets | DN# % | % DNVα24⁺ in total lymphocytes | Vα24JαQ DN sequence frequency | Vα24JαQ % |
|---|---|---|---|---|
| 1A/IL-4⁺ | 0.74 | 0.04 | 20/22 | 0.036 |
| 1B/IDDM | 0.95 | 0.01 | 10/19 | 0.005 |
| 1C/IDDM | 0.76 | 0.04 | 9/22 | 0.016 |
| 2A | 2.1 | 0.37 | 9/10 | 0.33 |
| 2B/IDDM | 3.1 | 0.025 | 31/31 | 0.025 |
| 3A | 1.1 | 0.04 | 8/12 | 0.027 |
| 3B/IDDM | 1/89 | 0.01 | 5/15 | 0.003 |
| 4A | 1.21 | 0.02 | 4/13 | 0.006 |
| 4B/IDDM | 0.31 | 0.006 | 0* | 0 |
| 5A | 0.58 | 0.06 | 8/12 | 0.04 |
| 5B/IDDM | 0.98 | 0 | 0* | 0 |
| 6A/new IDDM | 0.89 | 0.03 | 7/26 | 0.008 |
| 6B/IDDM | 2.62 | 0.03 | 8/23 | 0.01 |
| brother/sister 7A/IL-4⁺ | 2.54 | 0.03 | 8/12 | 0.017 |
| 7B/IDDM | 1.08 | 0.005 | 0/18 | 0 |

The frequency of Vα24JαQ TCR sequences was determined by sorting all CD4⁻CD8⁻ αβTCR⁺ T cells, amplifying all Vα24 transcripts and sequencing the TCR CDR3 region; the percentage of cells that were invariant CD4⁻CD8⁻ Vα24JαQ in total mononuclear cells was calculated by multiplying the sequence frequency by the CD4⁻CD8⁻ Vα24⁺ % of total mononuclear cells determined by flow cytometry.
DN = CD4⁻CD8⁻.
*No Vα24 PCR products were detected in three attempts.
IL-4⁺ indicates subject with high serum IL-4.

All references cited are fully incorporated by reference. Having now fully described the invention, it will be understood by those of skill in the art that the invention may be performed within a wide and equivalent range of conditions, parameters, and the like, without affecting the spirit or scope of the invention or any embodiment thereof.

---

---

What is claimed is:

1. A method for determining the likelihood that a human subject has type 1 diabetes, comprising:
 a) isolating CD4$^-$CD8$^-$ V$\alpha$24J$\alpha$Q$^+$ T cells from said human subject;
 b) stimulanting said t cells with a T cell activating factor and determining the amount of IL-4 and IFN-$\gamma$ secreted by said CD4$^-$CD8$^-$ V$\alpha$24J$\alpha$Q$^+$ T cells;
 c) based upon the determination of step b), calculating the ratio of IL-4 to IFN-$\gamma$; and
 d) correlating the ratio determined in step c) with the likelihood that said human subject has type 1 diabetes, wherein said likelihood increases as said ratio decreases.

2. The method of claim 1, wherein said T cell activating factor is anti-CD3 antibody.

3. The method of claim 1, further comprising determining the serum level of IL-4 in said human subject.

4. The method of claim 1, wherein said V$\alpha$24J$\alpha$Q$^+$ T cells are isolated by flow cytometry.

5. The method of claim 1, wherein said IL-4 secretion and said IFN-$\gamma$ secretion are determined using ELISA assays.

* * * * *